US009018444B2

(12) United States Patent
Fukuzawa et al.

(10) Patent No.: US 9,018,444 B2
(45) Date of Patent: Apr. 28, 2015

(54) NON-DIFFUSING PLANT VIRUS VECTOR

(75) Inventors: Noriho Fukuzawa, Hokkaido (JP); Takeshi Matsumura, Hokkaido (JP); Noriko Itchoda, Hokkaido (JP); Takeaki Ishihara, Hokkaido (JP); Chikara Masuta, Hokkaido (JP)

(73) Assignees: National Institute of Advanced Industrial Science and Technology, Tokyo (JP); The Hokuren Federation of Agricultural Cooperatives, Sapporo-shi (JP); National University Corporation Hokkaido University, Sapporo-shi (JP)

( * ) Notice: Subject to any disclaimer, the term of this patent is extended or adjusted under 35 U.S.C. 154(b) by 425 days.

(21) Appl. No.: 13/057,818

(22) PCT Filed: Aug. 7, 2009

(86) PCT No.: PCT/JP2009/003816

§ 371 (c)(1), (2), (4) Date: Feb. 22, 2011

(87) PCT Pub. No.: WO2010/016278

PCT Pub. Date: Feb. 11, 2010

(65) Prior Publication Data

US 2011/0138497 A1 Jun. 9, 2011

(30) Foreign Application Priority Data

Aug. 8, 2008 (JP) ................................ 2008-206446

(51) Int. Cl.

| | |
|---|---|
| ***C12N 15/83*** | (2006.01) |
| ***C12N 15/33*** | (2006.01) |
| ***C12N 15/82*** | (2006.01) |
| ***C12N 15/86*** | (2006.01) |

(52) U.S. Cl.

CPC ............ *C12N 15/8203* (2013.01); *C12N 15/86* (2013.01); *C12N 2770/14043* (2013.01)

(58) Field of Classification Search

None

See application file for complete search history.

(56) References Cited

U.S. PATENT DOCUMENTS

2005/0026291 A1 2/2005 Fedorkin

FOREIGN PATENT DOCUMENTS

| | | | |
|---|---|---|---|
| EP | 1616959 | A1 | 1/2006 |
| JP | 2003525050 | | 8/2003 |
| WO | 0164922 | A2 | 9/2001 |
| WO | 03029457 | A1 | 4/2003 |
| WO | 2005001102 | A1 | 1/2005 |

OTHER PUBLICATIONS

Sanz et al. (2000) Arch. Virol. 145: 2387-2401.*

Matsuo et al. (2007) Planta 225: 277-286.*

Gleba et al. (2004) Curr. Opin. Plant Biol. 7: 182-188.*

Marillonnet et al. (2005) Nat. Biotechnol. 23: 718-723.*

English translation of Hotta, M. et al. (2007) "Virus Vector o Mochiita Kokoritsu Hatsugen System no Kaihatsu" Preprints of Biotechnology Symposium, Nov. 6, 2007. 25th: 95-96.

Japanese Office Action received in JP 2008-206446, mailed Nov. 20, 2012.

Kaplan, et al. (1995) "Complementation of Virus Movement in Transgenic Tobacco Expressing the Cucumber Mosaic Virus 3a Gene" Virology, 209:188-199.

Extended European Search Report received in EP09804765, issued Oct. 4, 2011.

Li, Q. et al. (2001) "Cucumber mosaic virus—Plant Interactions: Indentification of 3a Protein Sequences Affecting Infectivity, Cell-to-Cell Movement, and Long-distance Movement" MPMI, 14(3):378-385.

Sugiyama, Y. et al. (1995) "Systemic Production of Foreign Peptides on the Particle Surface of Tobacco Mosaic Virus" FEBS Letters 359, 247-250.

Fernandez-Fernandez, M.R. et al. (1998) "Development of an Antigen Presentation System Based on Plum Pox Potyvirus" FEBS Letters 427, 229-235.

Donson, J. et al. (1991) "Systemic Expression of a Bacterial Gene by a Tobacco Mosaic Virus-Based Vector" Proc. Natl. Acad. Sci. USA 88, 7204-7208.

Mori, M. et al. (1993) "mRNA Amplification System by a Viral Replicase in Transgenic Plants" FEBS Letters 336(1), 171-174.

Zhao, Y. et al. (2000) "Development and Evaluation of a Complementation-Dependent Gene Delivery System Based on Cucumber Mosaic Virus" Archives of Virology 145, 2285-2295.

Canto, T. et al. (1997) "Characterization of Cucumber Mosaic Virus. IV. Movement Protein and Coat Protein are Both Essential for Cell-to-Cell Movement of Cucumber Mosaic Virus" Virology 237, 237-248.

Matsuo, K. et al. (2007) "Development of Cucumber Mosaic Virus as a Vector Modifiable for Different Hosts Species to Produce Therapeutic Proteins" Planta 225, 277-286.

Baulcombe, D.C. et al. (1995) "Jellyfish Green Fluorescent Protein as a Reporter for Virus Infection" Plant J. 7(6), 1045-1053.

Wang, Z.D. et al (2003) "Positional Effect of Gene Insertion on Genetic Stability of a Clover Yellow Vein Virus-Based Expression Vector" J Gen Plant Pathol 69, 327-334.

Mitsuhara, I. et al. (1996) "Efficient Promoter Cassettes for Enhanced Expression of Foreign Genes in Dicotyledonoud and Monocotyledonous Plants" Plant Cell Physiol. 37(1), 49-59.

Murashige, T. et al. (1962) "A Revised Medium for Rapid Growth and Bio Assays with Tobacco Tissue Cultures" Physiologia Plantarum 15, 473-497.

(Continued)

*Primary Examiner* — David T Fox

*Assistant Examiner* — Steven Bernacki

(74) *Attorney, Agent, or Firm* — Suzannah K. Sundby, Esq.; Canady + Lortz LLP

(57) ABSTRACT

The present invention is to provide a novel non-diffusing plant virus vector wherein virus vector infection and proliferation are possible only in a recombinant plant transformed with a gene necessary for viral proliferation, thereby enabling avoidance of unintended diffusion of a recombinant virus, a selective and specific expression system therefor, and a method of expression thereof which comprises combining a non-diffusing virus vector lacking a gene involved in intercellular movement of a cucumber mosaic virus (CMV) genome and a transgenic plant transformed with the lacked gene involved in intercellular movement for the non-diffusing virus vector to establish infection and proliferation selectively and specifically in the transgenic plant.

5 Claims, 7 Drawing Sheets

(56) References Cited

OTHER PUBLICATIONS

Cooper, B. et al. (1996) "Short Communication: Cell-to-Cell Transport of Movement-Defective Cucumber Mosaic and Tobacco Mosaic Viruses in Transgenic Plants Expressing Heterologous Movement Protein Genes" Virology 216, 208-213.

Nagano, H. et al. (2001) "Conversion in the Requirement of Coat Protein in Cell-to-Cell Movement Mediated by the Cucumber Mosaic Virus Movement Protein" Journal of Virology 75(17), 8045-8053.

Nagano, H. et al. (1997) "Deletion of the C-Terminal 33 Amino Acids of Cucumber Mosaic Virus Movement Protein Enables a Chimeric Brome Mosaic Virus to Move from Cell to Cell" Journal of Virology 71(3), 2270-2276.

Suzuki, M. et al. (1991) "Functional Analysis of Deletion Mutants of Cucumber Mosaic Virus RNA3 Using an in Vitro Transcription System" Virology 183, 106-113.

Nagano, H. (1999) "The Cognate Coat Protein is Required for Cell-to-Cell Movement of a Chimeric Brome Mosaic Virus Mediated by the Cucumber Mosaic Virus Movement Protein" Virology 265, 226-234.

International Search Report received in PCT/JP2009/003816, Nov. 17, 2010.

Maithri M. K. Jayasekera, et al., "Enhancement of Catalytic Activity by Gene Truncation: Activation of L-Aspartase from *Escherichia coli*", Biochemical and Biophysical Research Communications, 1997, pp. 411-414, vol. 238.

Miki Nakazawa, et al., "Analysis of Functional Region by Gene Transfer", Gendai-Kagaku, Zoukan-Gou (Chemistry Today, Special Edition), 1996, pp. 73-78.

. Japanese Office Action for Japanese Patent Application No. 2008-206446, Reference No. 2008-002075, mailed Jul. 16, 2013.

* cited by examiner

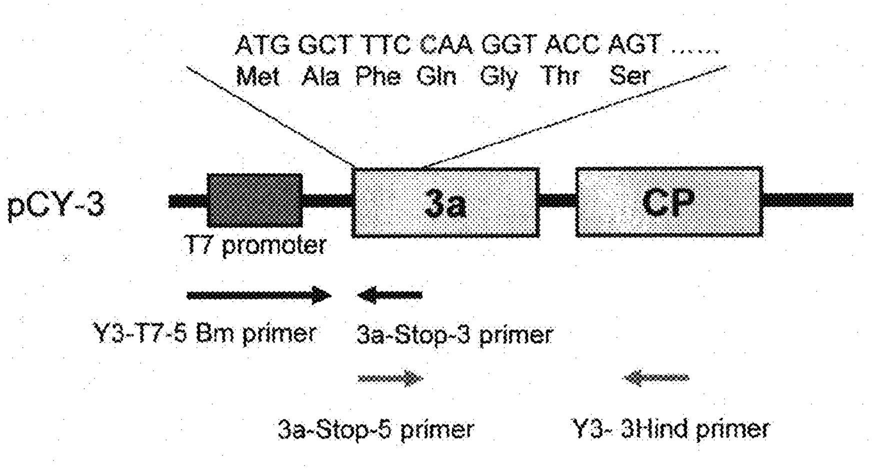

| | |
|---|---|
| Y3-T7-5Bm | CGGGATCCATTAATACGACTCACTATAGGTAATCTAACCACCTGT |
| 3a-Stop-3 | CTGGTACCTTAGAAAGCCAT |
| 3a-Stop-5 | ATGGCTTTCTAAGGTACCAG |
| Y3-3Hind | AACAAGCTTCTTATCATATTCC |

(THE DIAGONAL LINES SHOW THE CMV cDNA SEQUENCE AND THE DOUBLE UNDERLINED PART SHOWS T7 promoter SEQUENCE.
UNDERLINED PARTS IN Y3-T7-5Bm AND Y3-3Hind ARE RESTRICTION ENDONUCLEASE CLEAVAGE SITES, AND THE UNDERLINED PART IN 3a-Stop-3 AND 3a-Stop-5 ARE INTRODUCED MUTATIONS.)

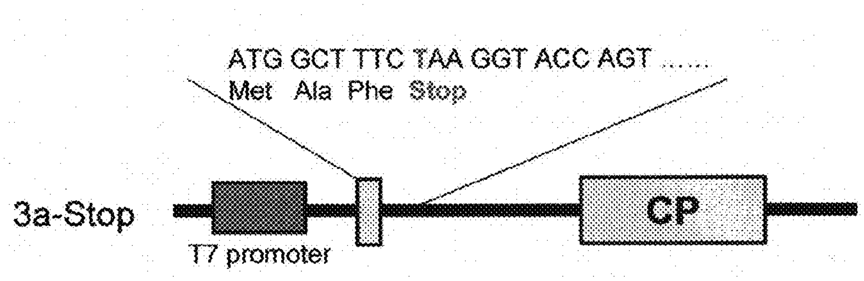

Fig. 1

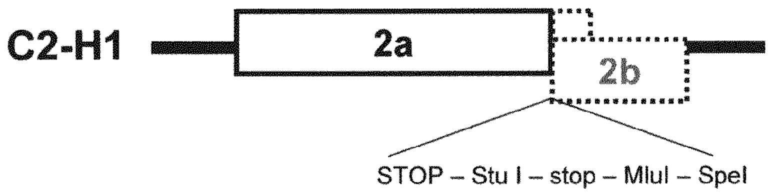
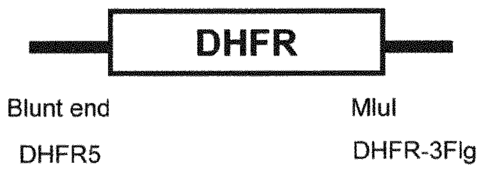
| | |
|---|---|
| DHFR5 | *ATGATCAGTCTGATTGCGG* |
| DHFR-3Flg | *GGCACGCGTCACTTGTCATCGTCGTCCTTGTAGTCCCGCCGCTCCAGAATCTCA* |
THE UNDERLINED PART IS A RESTRICTION ENDONUCLEASE CLEAVAGE SITE (MluI), AND THE DOUBLE UNDERLINED PART IS THE FLAG SEQUENCE.
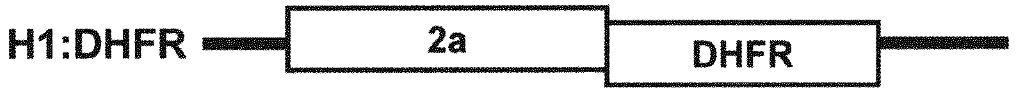
Fig. 2

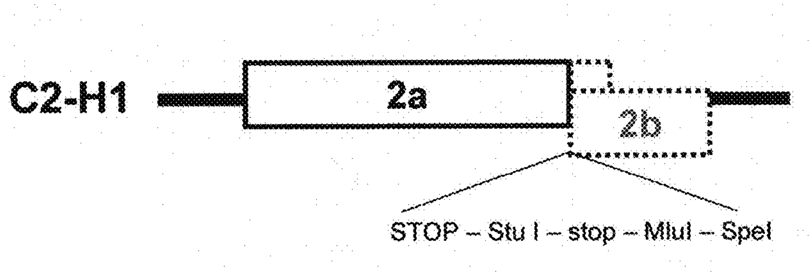
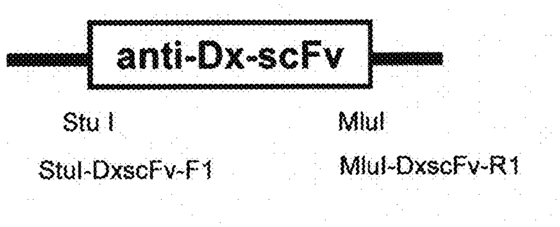
| | |
|---|---|
| StuI-DxscFv-F1 | *CGAGGCCTAGAATGTACTTGGGACTGAGC* |
| MluI-DxscFv-R1 | *GCGACGCGTTCAAAGTTCATCCTTATGATG* |
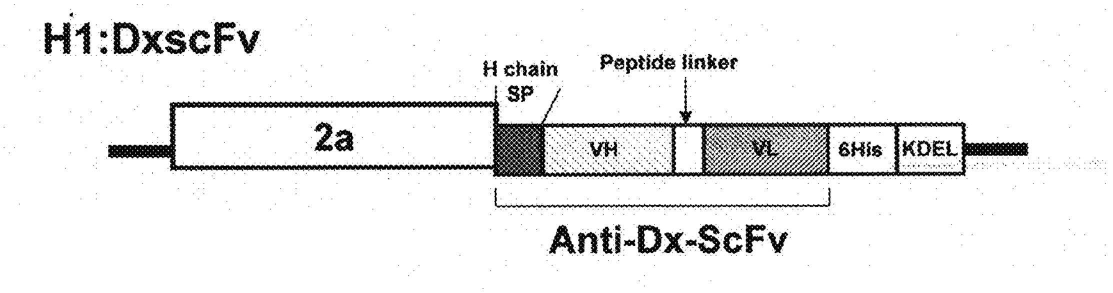
Fig. 3

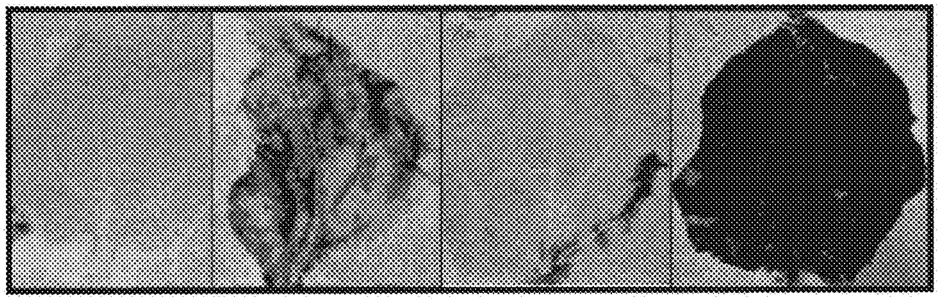
N. benthamiana INFECTED WITH THE ClYVV-3a vector WAS INOCULATED WITH Y1/Y2/3a-Stop, AND CMV WAS DETECTED BY Tissue printing 10 DAYS LATER.
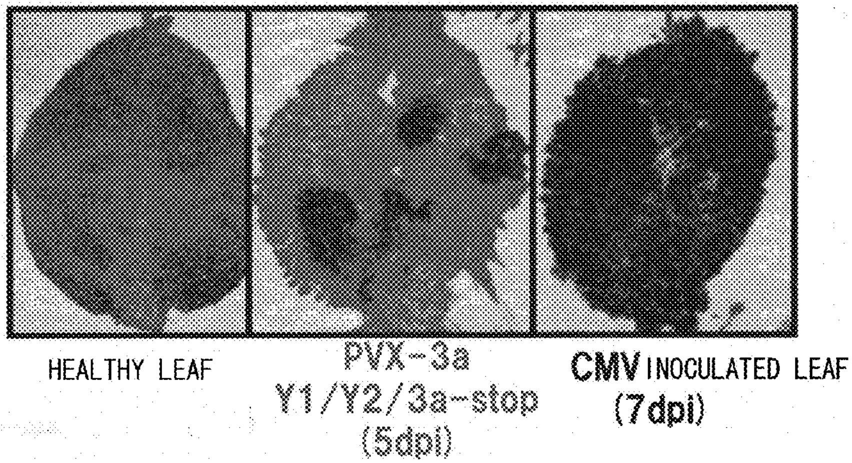
MIXED INOCULATION IN N. benthamiana WITH PVX-3a/Y1/Y2/3a-Stop WAS PERFORMED AND CMV WAS DETECTED BY Tissue printing.
Fig. 4

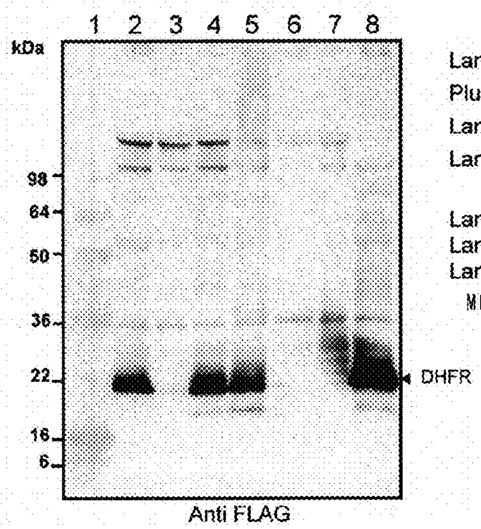

Lane1, molecular weight marker (SeeBlue(Trade Mark) Plus2 Prestained standard (1x) (invitrogen));
Lane2, Y1/H1:DHFR/Y3 INOCULATED LEAVES (positive control)
Lane3 AND 4, PVX-3a/Y1/H1:DHFR/Y3 MIXED INOCULATION (6dpi) INOCULATED LEAVES DIFFERENT INDIVIDUALS
Lane5, Y1/H1:DHFR/Y3 UPPER LEAVES (positive control)
Lane6, PVX/Y1/H1:DHFR/3a-Stop(negative control)
Lane7 AND 8, PVX-3a/Y1/H1:DHFR/3a-Stop MIXED INOCULATION (12dpi) UPPER LEAVES DIFFERENT INDIVIDUALS

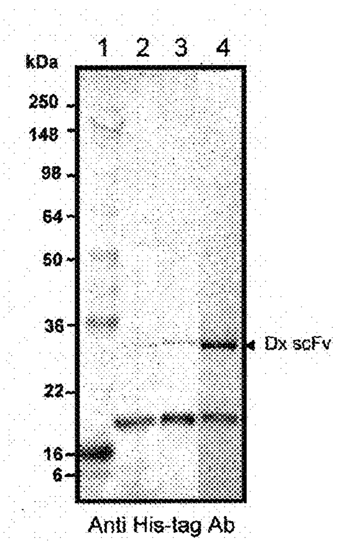

Lane1, molecular weight marker (SeeBlue(Trade Mark) Plus2 Prestained standard (1x) (invitrogen));
Lane2, Y1/H1:DxscFv/Y3 INOCULATED LEAVES (7dpi)(positive control);
Lane3 and 4, PVX-3a/Y1/H1:DxscFv/3a-Stop INOCULATED LEAVES (7dpi) AND UPPER LEAVES (7dpi)

Fig. 5

NON-DIFFUSING PLANT VIRUS VECTOR

TECHNICAL FIELD

The present invention relates to a non-diffusing plant virus vector, and more particularly to a non-diffusing plant virus vector that cannot proliferate when inoculated into a normal plant and is capable of proliferating only in a plant expressing a protein necessary for intercellular movement as a result of transfecting the plant separately with a plant virus vector lacking a viral gene involved in plant intercellular movement and with a vector carrying the aforementioned gene of the protein necessary for intercellular movement; a selective and specific plant virus vector expression system using the same; and a method of expression using the same. The present invention provides a non-diffusing plant virus vector, a selective and specific plant virus vector expression system using the same, and a method of expression using the same, thereby preventing uncontrolled diffusion of the virus vector by soil-borne, insect-borne, and direct-contact transmission.

BACKGROUND ART

In the past, research on RNA virus vectors has been carried out using infectious clones of the tobacco mosaic virus (TMV) and bromo mosaic virus (BMV), which have extremely high proliferative capability in infected plants. In this field several strategies for expressing foreign genes have been developed in the past because of differences in viral gene expression patterns, etc.

As an introduction to such strategies, for example, protein expression vectors prepared by fusion of a virus coat protein (CP) gene and a foreign gene have been developed using TMV and potyvirus (see non-patent documents 1 and 2). In addition, a vector expressing a foreign gene via a subgenome has been developed by transfection of a subgenomic promoter of TMV and a closely related virus (Odontoglossum ringspot virus) (see non-patent document 3).

However, rod-shaped and filamentous viruses typified by TMV and the family Potyviridae have primarily been used in the development of such virus vectors. That is because compared with spherical viruses, rod-shaped and filamentous virus vectors have the advantage of fewer physical limitations in the length of the foreign gene to be inserted. As an expression vector system using BMV, which is a spherical virus, a method has been reported wherein an RNA-3 derivative carrying a foreign gene was inoculated into tobacco expressing the replicase genes for protein 1a and protein 2a (see non-patent document 4).

Several studies using a cucumber mosaic virus (CMV) vector have also been conducted. In one such study a four-component CMV vector was developed by complementation (see non-patent document 5). It was found that both the movement protein (MP) and coat protein (CP) are encoded by RNA-3 of the CMV, and that both MP and CP are essential for intercellular movement of the virus (see non-patent document 6).

The inventors have already modified the RNA-3 molecule to construct an RNA-3A component wherein the MP region was replaced by the green fluorescent protein (GFP) gene and an RNA-3B component from which the CP gene was deleted, and thereby they have developed a virus vector capable of intercellular movement by complementation. When this vector was inoculated into *Nicotiana benthamiana* plants as a CMV having a virus genome consisting of the four components RNA-1, RNA-2, RNA-3A and RNA-3B, GFP fluorescence was observed in the minor veins of inoculated leaves.

In addition, when multiple cloning sites were inserted into the CP region that had been deleted in RNA-3B, and the GUS (bacterial-β-glucuronidase) gene and the bean yellow mosaic virus (BYMV) CP gene were inserted thereinto, GUS activity and the BYMV-CP were detected in the minor veins of inoculated leaves. However, homologous RNA recombination occurred between components RNA-3A and RNA-3B, and no systemic expression of the inserted genes was found.

In addition, as prior art various related techniques have been developed such as the production of various proteins by CMV vectors that can be used in a variety of different host plants (non-patent documents 7-11).

Non-patent document 1: Sugiyama, Y., Hamamoto, H., Takemoto, S., Watanabe, Y. and Okada, Y., Systemic production of foreign peptides on the particle surface of Tobacco mosaic virus, FEBS Letters 359, 247-250 (1995)

Non-patent Document 2: Fernandez-Fernandez, M. R., Martinez-Torrecuadrada, J. L., Casal, J. I. and Garcia, J. A., Development of an antigen presentation system based on plum pox potyvirus, FEBS Letters 427, 229-235 (1998)

Non-patent Document 3: Donson et al., Systemic expression of a bacterial gene by a tobacco mosaic virus-based vector, Proc. Natl. Acad. Sci. USA 88:7204-7208 (1991)

Non-patent Document 4: Mori, M., Kaido, M., Okuno, T. and Furusawa, I., mRNA amplification system by viral replicase in transgenic plants, FEBS Letters 336, 171-174 (1993)

Non-patent Document 5: Zhao, Y., Hammond, J., Tousignant, M. E., and Hammond, R. W., Development and evaluation of a complementation-dependent gene delivery system based on Cucumber mosaic virus, Archives of Virology 145, 2285-2295 (2000)

Non-patent Document 6: Canto, T., Prior, D. A., Hellward K. H., Oparka, K. J., Palukaitis, P., Characterization of cucumber mosaic virus. IV. Movement protein and coat protein are both essential for cell-to-cell movement of cucumber mosaic virus, Virology 237, 237-248 (1997)

Non-Patent Document 7: Matsuo, K., Hong, J. S., Tabayashi, N., Ito, A., Masuta, C., Matsumura, T. Development of Cucumber mosaic virus as a vector modifiable for different host species to produce therapeutic proteins. Planta 225: 277-286 (2007)

Non-Patent Document 8: Baulcombe, D C., Chapman, S., Santa Cruz, S. Jellyfish green fluorescent protein as a reporter for virus infections. Plant J 7:1045-1053 (1995)

Non-Patent Document 9: Wang, Z. D., Ueda, S., Uyeda, I., Yagihashi, H., Sekiguchi, H., Tacahashi, Y., Sato, M., Ohya, K., Sugimoto, C., Matsumura, T. Positional effect of gene insertion on genetic stability of a clover yellow vein virus-based expression vector. J Gen Plant Pathol 69:327-334 (2003)

Non-Patent Document 10: Mitsuhara, I., Ugaki, M., Hirochika, H., Ohshima, M., Murakami, T., Gotoh, Y., Katayose, Y., Nakamura, S., Honkura, R., Nishimiya, S., Ueno, K., Mochizuki, A., Tanimoto, H., Tsugawa, H., Otsuki, Y., Ohashi, Y. Efficient promoter cassettes for enhanced expression of foreign genes in dicotyledonous and monocotyledonous plants. Plant Cell Physiol 37:49-59 (1996)

Non-Patent Document 11: Murashige, T., Skoog, F. A revised medium for rapid proliferation and bio assays with tobacco tissue cultures. Physiol Plant 15(3), 473-497 (1962)

DISCLOSURE OF THE INVENTION

Under such circumstances and with the foregoing prior art in mind, the inventors conducted diligent and incisive research with the goal of developing a novel, non-diffusing plant virus vector capable of reliably solving the problems seen with previous plant virus vectors that establish uncontrolled infection in host plants, thereby resulting in unintended diffusion of recombinant virus genes. Thus, the inventors successfully developed a novel, non-diffusing plant virus vector that is capable of infection and proliferation only in specific transgenic plants expressing a protein involved in the intercellular movement of the virus in plants so that an unintended and uncontrolled spread of infection by the virus vector does not occur, thereby completing the present invention. An object of the present invention is to provide a novel, non-diffusing virus vector wherein an unintended and uncontrolled spread of infection thereof by soil-borne, insect-borne, and direct-contact transmission does not occur. A further object of the present invention is to provide a technique for using a plant to produce a substance by utilizing the above non-diffusing plant virus vector in combination with a specific transgenic plant wherein a protein necessary for intercellular movement in the plant is expressed by separate means.

All prior art plant virus vectors establish uncontrolled infection in the host plants, which results in unintended diffusion of the recombinant virus genes, and the risk of transmission of infection by insects is particularly high. Therefore, a further object of the present invention is to provide the first system for the selective and specific expression of plant virus vectors that enables infection and proliferation of the virus vector only in specific transgenic plants transformed with a gene involved in virus proliferation, and thereby enables the prevention of unintended spread of the recombinant virus by insects and by direct contact.

The technical means for solving the above problems in the present invention comprises the following items.

(1) A plant virus vector that is a non-diffusing plant virus vector lacking a gene involved in intercellular movement of a cucumber mosaic virus (CMV) genome, the plant virus vector being a CMV vector which lacks, through insertion of a stop codon, an RNA-3 gene encoding a 3a protein that is necessary for intercellular movement of a cucumber mosaic virus (CMV) in a plant, and which does not express a 3a protein of a 3a gene product, and the plant virus vector having an effect of establishing infection and proliferation selectively and specifically in a transgenic plant transformed with the gene involved in intercellular movement.

(2) The plant virus vector according to (1) above, wherein infection and proliferation are not established in a plant that has not been transformed with the gene involved in intercellular movement as a foreign gene.

(3) A system for a selective and specific expression of a plant virus vector, wherein a non-diffusing plant virus vector lacking a gene involved in intercellular movement of a cucumber mosaic virus (CMV) genome and a transgenic plant transformed with the lacked gene involved in intercellular movement are combined for the non-diffusing plant virus vector to establish infection and proliferation selectively and specifically in the transgenic plant, the non-diffusing plant virus vector lacking a gene involved in intercellular movement of a cucumber mosaic virus (CMV) genome is a CMV vector which lacks, through insertion of a stop codon, an RNA-3 gene encoding a 3a protein that is necessary for intercellular movement of a cucumber mosaic virus (CMV) in a plant, and which does not express a 3a protein of a 3a gene product, and the transgenic plant transformed with the gene involved in intercellular movement is a transformant transformed with an RNA-3 gene encoding a 3a protein necessary for intercellular movement of a cucumber mosaic virus (CMV) in a plant.

(4) The system for a selective and specific expression of a plant virus vector according to (3) above, wherein the gene involved in intercellular movement is a gene involved in movement of a virus by expansion of a plant intercellular plasmodesmata system or by association with a virus genome.

(5) The system for a selective and specific expression of a plant virus vector according to (3) above, wherein the transformant transformed with the gene involved in intercellular movement is a transformant transformed with a recombinant vector into which the gene involved in intercellular movement has been inserted as a foreign gene.

(6) The system for a selective and specific expression of a plant virus vector according to (3) above, wherein the non-diffusing plant virus vector does not establish infection and proliferation in a plant that has not been transformed with the gene involved in intercellular movement as a foreign gene.

(7) A method for a selective and specific expression of a plant virus vector, which comprises combining a non-diffusing plant virus vector lacking a gene involved in intercellular movement of a cucumber mosaic virus (CMV) genome and a transgenic plant transformed with the lacked gene involved in intercellular movement are combined for the non-diffusing plant virus vector to establish infection and proliferation selectively and specifically in the transgenic plant, the non-diffusing plant virus vector lacking a gene involved in intercellular movement of a cucumber mosaic virus (CMV) genome is a CMV vector which lacks, through insertion of a stop codon, an RNA-3 gene encoding a 3a protein that is necessary for intercellular movement of a cucumber mosaic virus (CMV) in a plant, and which does not express a 3a protein of a 3a gene product, and the transgenic plant transformed with the gene involved in intercellular movement is a transformant transformed with an RNA-3 gene encoding a 3a protein necessary for intercellular movement of a cucumber mosaic virus (CMV) in a plant.

(8) The method for a selective and specific expression of a plant virus vector according to (7) above, wherein the transformant transformed with the gene involved in intercellular movement is a transformant transformed with a recombinant vector into which the gene involved in intercellular movement has been inserted as a foreign gene.

(9) The method for a selective and specific expression of a plant virus vector according to (7) above, wherein the non-diffusing plant virus vector does not establish infection and proliferation in a plant that has not been transformed with the gene involved in intercellular movement as a foreign gene.

(10) A method for a selective and specific expression of a plant virus vector, which comprises combining a non-diffusing plant virus vector lacking a gene involved in intercellular movement of a cucumber mosaic virus (CMV) genome and a transgenic plant transformed with the lacked gene involved in intercellular movement for the non-diffusing plant virus vector to establish infection and proliferation selectively and specifically in the transgenic plant.

(11) The method for a selective and specific expression of a plant virus vector according to (10) above, wherein the non-diffusing plant virus vector lacking a gene involved in intercellular movement of a cucumber mosaic virus (CMV) genome is a CMV vector which lacks an RNA-3 gene encoding a 3a protein necessary for intercellular movement of a CMV in a plant, and which does not express a 3a gene product.

(12) The method for a selective and specific expression of a plant virus vector according to (10) above, wherein the transgenic plant transformed with the gene involved in intercellular movement is a transformant transformed with the RNA-3 gene encoding a 3a protein necessary for intercellular movement of a cucumber mosaic virus (CMV) in a plant.

(13) The method for a selective and specific expression of a plant virus vector according to (10) above, wherein the transformant transformed with the gene involved in intercellular movement is a transformant transformed with a recombinant vector into which the gene involved in intercellular movement has been inserted as a foreign gene.

(14) The method for a selective and specific expression of a plant virus vector according to (10) above, wherein the non-diffusing plant virus vector does not establish infection and proliferation in a plant that has not been transformed with the gene involved in intercellular movement as a foreign gene.

The present invention is explained in greater detail below.

The present invention is a non-diffusing plant virus vector lacking a gene involved in intercellular movement of the cucumber mosaic virus (CMV) genome, and the plant virus vector has the effect of establishing infection and proliferation selectively and specifically in a transgenic plant transformed with the above gene involved in intercellular movement. In the present invention, the gene involved in intercellular movement of the cucumber mosaic virus (CMV) genome is defined as a gene in the plant virus genome that encodes a protein that can expand a molecular weight exclusion limit of the gating capacity of plasmodesmata (intercellular bridges that connect adjacent cells in higher plants) to enable the virus genome to move to an adjacent cell (cell-to-cell movement protein).

The present invention is also a system for the selective and specific expression of the above plant virus vector wherein a non-diffusing plant virus vector lacking a gene involved in intercellular movement of the cucumber mosaic virus (CMV) genome is used in combination with a transgenic plant transformed with that lacked gene involved in intercellular movement, and the above non-diffusing plant virus vector establishes infection and proliferation selectively and specifically in the above transgenic plant.

Furthermore, the present invention is a method for the selective and specific expression of the above plant virus vector wherein a non-diffusing plant virus vector lacking a gene involved in intercellular movement of the cucumber mosaic virus (CMV) genome is used in combination with a transgenic plant transformed with that lacked gene involved in intercellular movement, and the above non-diffusing plant virus vector establishes infection and proliferation selectively and specifically in the above transgenic plant.

A preferred aspect of the present invention is one wherein the above plant virus vector is a CMV vector which lacks the RNA-3 gene encoding the 3a protein necessary for intercellular movement of the cucumber mosaic virus (CMV) in a plant, and which does not express the 3a gene product, or one wherein the non-diffusing plant virus vector which lacking the above gene involved in intercellular movement of the cucumber mosaic virus (CMV) genome is a CMV vector which lacks the RNA-3 gene encoding the 3a protein necessary for intercellular movement of the cucumber mosaic virus (CMV) in a plant, and which does not express the 3a gene product.

In addition, a preferred aspect of the present invention is one wherein the transgenic plant transformed with the above gene involved in intercellular movement is a transformant transformed with the RNA-3 gene encoding the 3a protein necessary for intercellular movement of the cucumber mosaic virus (CMV) in a plant, and the transformant transformed with the above gene involved in intercellular movement is also a transformant transformed with a recombinant vector into which the above gene involved in intercellular movement has been inserted as a foreign gene.

In the present invention, a plant virus vector has been constructed so that the genetic information in the genome necessary for a plant virus to move from cell to cell within an infected plant has been deleted therefrom. Thus, the virus acts only on a transgenic plant that expresses the gene necessary for intercellular movement. The virus vector is capable of moving and proliferating as a whole only when this transgenic plant is inoculated with the plant virus vector, but the virus vector does not proliferate in other plants and the transmission thereof to other plants does not occur because the gene product necessary for intercellular movement is missing.

With previous virus vectors, infection can spread uncontrollably to other host plants after inoculation and infection of the plant. A virus (vector) cannot proliferate in an inoculated plant if the gene necessary for the migration thereof throughout an infected plant has been deleted. The above virus vector can proliferate, however, in a transgenic plant transformed with the lacked gene necessary for migration, or in a plant transformed with that gene by another virus vector. However, the above virus vector cannot proliferate in a normal plant, so the infection cannot spread uncontrollably as in previous virus vectors.

In the present invention, a plant virus vector incapable of intercellular movement has been constructed. A cucumber mosaic virus vector (CMV vector) is used as the plant virus vector. The gene product necessary for intercellular movement of the CMV in a plant is the CMV 3a protein encoded by RNA-3, and this CMV 3a protein is involved in intercellular movement. Therefore, a Δ3a CMV vector lacking the 3a gene of the CMV vector was constructed, and as a result, it did not express the 3a gene product.

When the 3a protein, which is the gene product in the CMV, invades plant cells, the gating capacity of plasmodesmata to adjacent cells expands, enabling movement of the virus from cell to cell. Because a CMV vector lacking the 3a protein gene of the CMV cannot expand plasmodesmata gating capacity, cell-to-cell movement of the virus becomes impossible, the virus does not spread to the entire plant, and uncontrollable diffusion of the virus does not occur. This property alone, however, is not useful as a vector.

Therefore, the inventors constructed a vector that does express the 3a protein of the CMV as a different virus vector to enable the proliferation and intercellular movement of the Δ3a CMV vector, and they conducted tests verifying infection by the Δ3a CMV vector in plants by tissue printing. As a result, it was found that the 3a protein supplied by another virus vector functions in trans, and enables both movement of the Δ3a CMV vector as a whole and expression of a target substance (anti-Dx antibody) thereby.

Next, to develop a transgenic plant for the CMV (Δ3a) wherein even the vector lacking the 3a protein (i.e., Δ3a) becomes capable of intercellular movement, mixed inoculation of tobacco plants was conducted using the Δ3a CMV vector and another vector carrying the CMV 3a gene. As a result, it was found that in the 3a-transformed tobacco the Δ3a CMV vector was capable of systemic migration throughout the plant. From this it was learned that a plant virus vector lacking a gene involved in intercellular movement of the virus cannot proliferate on its own, and it cannot diffuse or spread, but systemic infection with the Δ3a CMV vector becomes possible by separate transformation with a protein enabling intercellular movement, and the Δ3a CMV vector then becomes functional.

The plant virus vector that was actually used is a cucumber mosaic virus vector (CMV vector). The gene necessary for intercellular movement in this virus is the 3a protein encoded by RNA-3. Therefore, the inventors constructed a CMV vector that does not express the 3a gene product, i.e., the Δ3a CMV vector. The inventors also verified that no infection was found when this vector alone is inoculated into a host plant (tobacco).

On the other hand, when the 3a gene of the CMV was incorporated into a different virus vector, and mixed inoculation of tobacco was performed using both that vector and the Δ3a CMV vector, systemic infection was found. More specifically, when the 3a gene of the CMV was inserted into a clover yellow vein virus vector (ClYVV vector), etc., and mixed inoculation of that vector and the Δ3a CMV vector was performed in tobacco, systemic infection was found. In other words, the Δ3a CMV vector moved from cell to cell and established systemic infection because the 3a protein of the CMV was supplied in trans in the inoculated plants by a non-CMV virus vector.

These results proved the technical concept of the present invention that a plant virus vector lacking a gene involved in intercellular movement of the virus cannot proliferate on its own, i.e., it cannot diffuse and spread on its own, but systemic infection thereby becomes possible by supplying the protein necessary for intercellular movement in the plant by separate means and imparting functionality to the vector thereby.

In addition, when a recombinant tobacco plant transformed with the 3a protein gene was prepared and then inoculated with the Δ3a CMV vector, intercellular movement of the virus vector and systemic infection were confirmed. These results proved that if the Δ3a CMV vector is inoculated into a normal plant it cannot proliferate, and it can proliferate only in plants expressing the 3a protein. In other words, uncontrollable diffusion of the virus vector does not occur with the Δ3a CMV vector alone.

The present invention relates to a non-diffusing plant virus vector and a system for the selective and specific expression of a non-diffusing plant virus vector wherein the non-diffusing plant virus vector is used in combination with a specific transgenic plant. Just as in genetic engineering technology, the present invention is not restricted to an individual vector or species of host plant, and is a general, universal, and broadly applicable technique provided the plant virus vector spreads via insects, direct contact, and the like. Therefore, the plant virus vector that spreads via insects, direct contact, and the like and the species of host plant are not particularly limited in the present invention.

The invention specifically relating to the method for transforming a plant using the non-diffusing plant virus vector of the present invention provides, as a method invention, a novel technical concept of preventing the establishment of uncontrolled infection in a host plant by a plant virus vector and the unintended diffusion of a recombinant viral gene by using the non-diffusing plant virus vector in combination with the specific transgenic plant set forth in the present invention. Therefore, this is a broadly applicable, general technique that is not limited to an individual type of plant virus vector that spreads via insects, direct contact, and the like, or to a specific species of transgenic plant. Yet, as shown in the examples presented below, concrete proof of the establishment of a selective and specific system for infection and proliferation using a non-diffusing plant virus vector and a transgenic plant is presented in the present invention through the use of a cucumber mosaic virus vector (CMV vector) as the plant virus vector. The present invention is applied herein to a CMV vector, but is likewise applicable to other plant virus vectors as a mode of use for a plant virus vector.

With previous virus vectors, the unintended spread of infection by the virus vector from an infected plant inoculated therewith was unavoidable. Because infection and proliferation in the present invention are possible only in a transgenic plant expressing a protein involved in viral movement (the CMV 3a protein), unintended spread of infection by the virus vector does not occur. In other words, because diffusion does not occur even if the virus vector is used outdoors, etc., a dramatic expansion of the scope of use of virus vectors becomes possible thereby.

The present invention provides the following advantageous Effects:

(1) The present invention can provide a non-diffusing plant virus vector enabling the prevention of uncontrolled infection of host plants and the risk of unintended diffusion of a recombinant virus;

(2) The present invention can provide a new transgenic plant system enabling the prevention of untended diffusion of a virus because infection and proliferation of the virus vector is possible only in transgenic plants transformed with a gene necessary for viral proliferation;

(3) The present invention can provide a non-diffusing plant virus vector that cannot diffuse or spread by itself, but becomes capable of systemic infection and functional as a virus through the separate introduction of a gene encoding a protein necessary for intercellular movement thereof;

(4) The present invention dramatically expands the scope of use of plant virus vectors because the plant virus vectors do not diffuse even when used outdoors, etc.; and (5) The present invention enables planning for the use of a plant virus vector with guaranteed safety because proliferation of the virus vector and the spread to other plants does not occur even when a transgenic plant is prepared using the plant virus vector of the present invention.

BRIEF DESCRIPTION OF THE DRAWINGS

FIG. 1 shows the process for preparing a vector lacking the 3a gene (3a-Stop) by substituting a TAA codon, which is a stop codon, for the CAA codon encoding the amino acid glutamine at position 4 in the 3a protein of pCY3; the sequences from top to bottom are SEQ ID NOs:13-18;

FIG. 2 shows the process for transferring a foreign gene by inserting a foreign gene (DHER) sequence between the StuI site and MluI region of a C2-H1 vector; the sequences from top to bottom are SEQ ID NOs:19-20;

FIG. 3 shows the process for transferring a foreign gene (DxscFv) into CMV-Y RNA-2 by inserting the DxscFv sequence between the StuI site and MluI region of a C2-H1 vector; the sequences from top to bottom are SEQ ID NOs: 21-22;

FIG. 4 shows the results of tissue printing using ClYVV-3a/Y1/Y2/3a-Stop and PVX-3a/Y1/Y2/3a-Stop;

FIG. 5 shows detection of DHFR and DxscFv by western. blot 6 to 12 days after mixed inoculation of wild-type *Nicotiana benthamiana* with RNA transcripts PVX-3a/Y1/H1: DHFR (or H1:DxscFv)/3a-Stop;

BEST MODE FOR CARRYING OUT THE INVENTION

Figure 6:
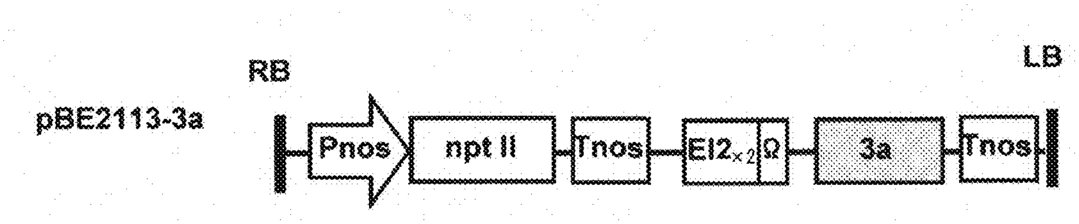
FIG. 6 shows the process of transferring the intercellular movement protein (3a) to pBE2113 by inserting the sequence of the 3a protein from CMV-Y3a between the XbaI site and Sad region of pBE2113, which is a plant expression vector.

Next the present invention is explained in detail based on an example, but the present invention is by no means limited thereto.

EXAMPLES

(1) Raising of Wild-Type Plant Specimens

*Nicotiana benthamiana* plants were raised in the following manner. After Jiffy-7 peat pellets (Sakata Seed Corporation) were soaked in water, they were sown with 2 to 3 seeds per pot, and kept under warm conditions. After culling to align the growth stage of the plants, the remaining sprouts were raised at an air temperature of 28° C. under 12 hours of light (8,000 lux) and 12 hours of darkness. Fertilizer was applied thereafter as the plants grew.

(2) Raising of Plants Used for Vector Proliferation

Raising of *Vicia faba* plants used for proliferation of the CIYVV vector was carried out using potting medium (Sankyo). The medium was placed in No. 4 pots, wetted sufficiently, and 1 seed per pot was sown. The plants were used for inoculation 10 days after sprouting.

(3) Inoculation test

*N. bemthamiana* individuals 3 to 4 weeks after sowing wherein 3 to 5 true leaves had opened were used for inoculation. Either crude liquid from the upper leaves of plants with obvious signs of mosaic, leaf curl, or another viral infection, or reverse-transcribing RNA was used as the inoculum. In plants that had reached the inoculation stage, whole leaves to be inoculated were lightly sprinkled with carborundum (Nacalai Tesque, #600 mesh dried). The crude liquid for viral inoculation was prepared by adding DIECA (sodium N,N-diethyldithiocarbamate, Wako Pure Chemical) to 1 mL of 0.1 M phosphate buffer (pH 8.0) immediately before inoculation to make a final concentration of 10 mM, and pulverizing the same by mortar and pestle together with 0.1 g of infected leaves serving as the inoculum.

The reverse-transcribing RNA for inoculation was synthesized by the method described below and prepared by adding an equivalent amount of 0.1 M potassium phosphate buffer (pH 8.0) to the total amount thereof. For both inoculations the inoculum was applied to a latex finger sac and then spread gently on the surface of the leaves with the fingertip. Immediately after inoculation the excess crude liquid and carborundum were rinsed from the surface of the leaves, and the leaves were kept in the dark until the next day. To prepare the 0.1 M potassium phosphate buffer, 0.1 M dibasic potassium phosphate and 0.1 M monobasic potassium phosphate were mixed together, and the pH was then adjusted to 8.0.

(4) Preparation of Competent Cells

*E. coli* strain JM109 (TaKaRa Bio, Inc.) was added to 2 mL of the SOB liquid culture medium described below and cultured for 12 to 14 hours at 37° C. Then 0.5 mL of the above culture liquid was added to 50 mL of SOB liquid culture medium described below and shaking culture was performed for approximately 1.5 hours at 37° C. ($OD_{550}$=0.4 to 0.8). After the culture was placed on ice for 10 min, it was transferred to a tube and centrifuged for 10 min at 3,500 rpm and 4° C. Then the supernatant was discarded, and the precipitate was gently suspended in 17 mL of ice cold TFB described below.

After the suspension was let stand on ice for 20 min, it was centrifuged again for 10 min at 3,500 rpm and 4° C. The supernatant was discarded, 2 mL of ice cold TFB were added, and the precipitate was gently suspended on the surface of the liquid. After the suspension was let stand on ice for 30 min, 150 μL of DMSO (dimethyl sulfoxide, Nacalai Tesque) was slowly added drop by drop, and the suspension was again let stand on ice for 10 min. Finally, 100 μL aliquots were placed in 1.5 mL tubes using a thick-tipped pipette, and the tubes were frozen and stored at −80° C.

The SOB liquid culture medium was prepared by mixing 20 g of Bacto™ Tryptone (Becton Dickinson) and 5 g Bacto™ Yeast Extract (Becton Dickinson) in 10 mL of 1 M NaCl solution together with 2.5 mL of 1 M KCl solution, raising the volume to 1 L with distilled water, and sterilizing by autoclave. Then immediately before use 1/100 volumes of filter-sterilized 1 M $MgCl_2$ solution (Nacalai Tesque) and 1 M $MgSO_4$ solution (Nacalai Tesque) were added.

The TFB (transformation buffer solution) was prepared by making a composition of 35 mM potassium acetate (Nacalai Tesque), 50 mM $CaCl_2$ (Wako Pure Chemical), 45 mM $MnCl_2$ (Nacalai Tesque), 100 mM RbCl (Nacalai Tesque), and 15% sucrose (Wako Pure Chemical)-acetic acid (Wako Pure Chemical), adjusting the pH to 5.8, and filter-sterilizing.

(5) Transformation

First 1 μL of plasmid (or about 5 μL in the case of a ligation reaction solution) was gently added to 100 μL of competent cells, let stand on ice for 30 min, and then mixed. The mixture was placed in a 42° C. water bath for 45 sec to perform a heat shock, and then it was immediately cooled on ice to transfer the recombinant plasmids into the *E. coli* cells. Then the 2YT liquid culture medium described below was added, and standing culture was performed for 30 min at 37° C. Next, shaking culture was performed for 1 hour at 37° C., and 100 μL of the culture solution was spread onto the LB-amp medium described below.

For performing blue-white selection first 50 μL of 2% X-gal (prepared by dissolving 5-bromo-4-chloro-3-indolyl-β-D-galactopyranoside (Wako Pure Chemical) to a concentration of 2% in N,N-dimethyl formamide (Nacalai Tesque)) and 10 μL of 100 mM IPTG (isopropyl-β-D(−)-galactopyranoside solution (Wako Pure Chemical, filter-sterilized) were spread on LB agar beforehand, and then the medium was inoculated with 100 μL of *E. coli* culture liquid. Culturing was performed for 12 to 16 hours in an incubator at 37° C.

The 2YT liquid culture medium was prepared by mixing 16 g of Bacto™ Tryptone, 10 g of Bacto™ Yeast Extract, and 10 g of NaCl, raising the volume to 1 L with distilled water, and autoclaving. The LB-amp medium was prepared by mixing 10 g of Bacto™ Tryptone, 5 g of Bacto™ Yeast Extract, 10 g of NaCl, and 15 g of Agar (Wako Pure Chemical), raising the volume to 1 L with distilled water, and autoclaving. Then when the preparation was allowed to cool to about 50° C., 1/1000 volume of 50 mg/mL ampicillin stock (Wako Pure Chemical, filter-sterilized) was added, and the medium was poured into sterile Petri dishes before it hardened.

(6) Plasmid Extraction

Colonies of *E. coli* obtained by transformation were lifted with a sterilized toothpick and placed into 2 mL of 2YT liquid culture medium to which 2 μL of 50 mg/mL ampicillin stock had been added, and shaking culture was performed for 12 to 14 hours at 37° C. The liquid culture medium was placed in a 1.5 mL tubes and centrifuged at 10,000 rpm for 3 min. The supernatant was removed with an aspirator, 100 μL of Solution-1 described below was added to each, and the precipitate was completely therein suspended using a tube mixer. Then 200 μL of Solution-2 described below was added to each, and the contents were mixed by inverting the tube.

Next, 150 μL of Solution-3 described below was added to each, and once again mixing was performed by inverting the tubes. The tubes were centrifuged at 14,000 rpm and 4° C. for 5 min, the supernatants were transferred to different tubes, and centrifugation (14,000 rpm, 5 min) was performed once more to completely remove proteins. The supernatants were transferred to different tubes, an amount of isopropyl alcohol (Wako Pure Chemical) equivalent to the amount of collected supernatant was added to each, and the contents were mixed by inverting the tubes. The mixtures were then centrifuged at 14,000 rpm for 5 min, and the supernatants were discarded. Next 500 μL of 80% ethanol (Nacalai Tesque) was added to the precipitates, the contents were centrifuged at 14,000 rpm for 5 min, and the supernatants were discarded. Then 50 μl of RNase A diluted to a final concentration of 2 μg/mL in TE (10 mM Tris-HCl (pH 7.5) and 1 mM EDTA (pH 8.0)) was added to each, and the contents were mixed gently with a mixer and let stand for 30 min at 37° C.

Next 30 μL of Solution-4 described below was added, the contents were mixed with a vortex mixer, and the tubes were let stand on ice for 45 min. The tubes were then centrifuged at 14,000 rpm for 10 min and the supernatants were discarded. Then 500 μL of 80% ethanol was added, and the tubes were centrifuged at 14,000 rpm for 5 min. The supernatants were discarded, and the precipitates were dried under vacuum for 5 to 10 min, and then suspended in 30 μl of sterile water. The resulting plasmid samples were stored at −30° C.

a) Solution-1:

25 mM Tris (2-amino-2-hydroxymethyl-1,3-propanediol) (Wako Pure Chemical)-HCl (pH8.0), 10 mM EDTA (ethylene diamine-N,N,N',N'-tetraacetacetic acid, Dojindo Laboratories), and 50 mM glucose (Wako Pure Chemical)

b) Solution-2:

0.2 N NaOH (Wako Pure Chemical), and 1% SDS (sodium lauryl sulfate, Nacalai Tesque)

c) Solution-3:

60 mL of 5 M potassium acetate solution, 11.5 mL of acetic acid, and 28.5 mL of distilled water d) Solution-4:

20% PEG #6000 (polyethylene glycol, Nacalai Tesque), and 2.5 M NaCl (7) Methods of basic genetic procedures 1) Restriction Enzyme Treatments The treatments were performed for at least 1 hour at the designated temperatures using 0.5 μL of restriction enzyme from the respective manufacturers in a 10 μL reaction system prepared with the accompanying buffer.

2) Electrophoresis

Electrophoresis was performed with a TBE (89 mM Tris-base, 89 mM boric acid (Wako Pure Chemical), 2 mM EDTA)-agarose gel (Genapure™ LE AGAROSE-BM) at a concentration suitable for the length of the target DNA and using TBE as the electrolysis buffer. After electrolysis, staining was performed with an ethidium bromide solution (final concentration 0.5 μg/mL).

3) Phenol-Chloroform Extraction

Sterile water was added to the sample DNA solution to make 100 μL. Then 50 μL of TE-saturated phenol (Nippon Gene) and 50 μL of chloroform (Wako) were added, and the tube was placed on a tube mixer and stirred for 1 min to deactivate the protein. Then the contents were centrifuged at 14,000 rpm for 5 min, and only the aqueous layer was transferred to a 1.5 mL tube.

4) Ethanol Precipitation

First 10 μL of 3 M sodium acetate (Nippon Gene) and 250 μL of 100% ethanol were added to 100 μL of the sample DNA solution and stirred. Then the contents were centrifuged at 14,000 rpm for 10 min and the supernatant was removed. Next, 500 μL of 80% ethanol was added, and the contents were centrifuged at 14,000 rpm for 5 min. The supernatant was removed, and the precipitate was dried under vacuum.

5) Cloning

When the DNA was recovered from the gel, SeaKem™ GTC™ agarose (BMA) was directly overlaid with agarose gel containing ethidium bromide at a final concentration of 0.5 μg/mL, and electrophoresis was performed. The section of gel containing the target band was cut out, and the DNA was recovered using QIAEX™ II Gel Extraction Kit 150 (QIAGEN).

After phenol-chloroform extraction and ethanol precipitation were performed on the solution of recovered DNA, the precipitate was suspended in 5 μl of sterile water. A DNA Ligation Kit <Mighty Mix> (TaKaRa Bio, Inc.) was used for vector-insert ligation. An equivalent volume of Ligation Mix was added to the solution of recovered DNA and the DNA was suspended. The suspension was let stand for 30 min at 16° C., and 5 μl of ligation reaction solution was added for transformation into *E. coli* competent cells.

(8) In Vitro Transcription of Infectious Clone

First 4 μL of infectious clone extracted with alkali-SDS was linearized with restriction enzymes using run-off transcription, extracted with phenol-chloroform, and precipitated with ethanol, and then the resulting pellet was suspended in 3.5 μL of sterile water. The transcription reaction solution was mixed in the following manner.

(Transcription Reaction Solution)

3.5 μL of template solution

2 μL of 50 mM DTT

2 μL of 0.1% BSA

2 μL of 10× T7 RNA polymerase Buffer*[11]

*11 . . . Packaged with the T7 RNA polymerase (TaKaRa Bio, Inc.)

8 μL of 2.5× Cap/NTP mix*[12]

*12 . . . 2.5× Cap/NTP mix (5 mM $m^7$ G (5')ppp (5')G RNA Capping Analog (Invitrogen), 3.8 mM ATP, 3.8 mM CTP, 3.8 mM UTP, 0.8 mM GTP-Roche)

0.5 μL of RNase inhibitor*[13]

*13 . . . Ribonuclease Inhibitor recombinant solution (Wako Pure Chemical)

2 μL of T7 RNA polymerase

The suspension was let stand for 2 hours at 37° C. RNA transcription was confirmed by electrophoresis. Unless inoculation was to be performed immediately, the transcription product was stored at −80° C.

(9) RNA Extraction (Phenol-SDS Method)

First 0.1 g of test sample was pulverized together with 500 μL of RNA extraction buffer and 500 μL of TE-saturated phenol, and that was transferred to a 1.5 mL tube. The tube was placed on a vortex mixer for about 20 sec and centrifuged under refrigeration at 14,000 rpm for 5 min. The supernatant (aqueous layer) was transferred to a separate tube, and a volume phenol-chloroform (1:1) equal to that of the supernatant was added. The tube contents were stirred vigorously with a vortex mixer and centrifuged under refrigeration at 14,000 rpm for 5 min, and the supernatant was transferred to a separate tube. The above phenol-chloroform extraction was performed repeatedly until the white protein layer had disappeared. Finally, after rinsing with an equal volume of phenol-chloroform, the aqueous layer was taken, and a 1/10 volume of 3 M sodium acetate and a 3-fold volume of 100% ethanol were added thereto.

The tube contents were mixed with a vortex mixer and centrifuged under refrigeration at 14,000 rpm for 5 min. The supernatant was discarded, 500 μL of 80% ethanol was added, and the tube contents were centrifuged under refrigeration at 14,000 rpm for 5 min. After the tube contents were dried under vacuum for 5 to 10 min, they were suspended in 50 μL of sterilized water for RNA, and the suspension was centrifuged at 14,000 rpm for 1 min. If a precipitate formed, only the supernatant was transferred to a separate tube. The RNA extraction buffer was a composition of 25 mM Tris-HCl (pH 7.5), 25 mM $MgCl_2$, 25 mM KCl, and 1% SDS.

(10) RT-PCR

1) Reverse Transcription Reaction

The following reaction solution was prepared.

7.5 μL of RNase Free $dH_2O$*[15]

4 μL of 25 mM $MgCl_2$*[15]

2 μL of each 10 mM dNTP Mixture*[15]

2 μL of 10× RNA PCR Buffer*[15]

*15 . . . Packaged with the RNA PCR™ kit (AMV) Ver. 2.1 (TaKaRa Bio, Inc.)

0.5 μL of RNase Inhibitor

1 μL of 3' primer

2 μL of sample RNA 0.5 μL of AMV Reverse Transcriptase XL (TaKaRa Bio, Inc.)

The reaction solution was let stand for 1 hour at 45° C. The reaction solution was boiled for 5 min and rapidly cooled for 5 min to deactivate the reverse transcriptase.

2) PCR Reaction

The following PCR mix was prepared.

8.4 μL of sterile water

2 μL of 25 mM $MgCl_2$*[16]

2 μL of 10× LA PCR™ Buffer II ($Mg^{2+}$ free)*[16]

*16: Packaged with TaKaRa LA Taq™

2 μL of each 10 mM dNTP Mixture 0.2 μL of 5' primer 0.2 μL of 3' primer

First 5 μL of the reverse transcription reaction solution was added to the PCR mix, and then 0.2 μL of TaKaRa LA Taq™ was added, and PCR was performed. Electrophoresis was performed on the PCR product using 1% agarose gel, and it was confirmed that the target fragment had been amplified.

(11) Sequences

When verifying a sequence using a plasmid as a template, 100 ng of sample extracted by the alkali-SDS method was used in the sequencing reaction. When direct sequencing was performed, 10 ng of target DNA recovered from the gel fragment was used in the sequencing reaction. A sample prepared by adding 1.3 μL of primer (1 pmol, Big Dye™ Terminator v1.1 Cycle sequencing kit (Applied Biosystems)) and 3.4 μL of the accompanying buffer to the template DNA and raising the volume to 20 μL was used as the sequencing reaction solution. PCR was performed under the following conditions.

1 cycle of [96° C., 1 min]

30 cycles of [96° C., 10 sec→50° C., 5 min→60° C., 4 min]

10° C. to infinity

After the PCR reaction 64 μL of 100□ ethanol and 16 μL of distilled water were added, the reaction mixture was let stand for 15 min at room temperature, and then centrifuged at 14,000 rpm for 15 min. The supernatant was removed, 250 μL of 80□ ethanol was added, and the mixture was centrifuged at 14,000 rpm for 10 min. The supernatant was removed, and the precipitate was air dried under vacuum. Then 25 μl of HiDi formamide (Applied Biosystems) was added, the precipitate was dissolved, denatured at 95° C. for 3 min, and annealed by cooling rapidly. The sample was mounted in an ABI PRISM' 310 Genetic Analyzer (Applied Biosystems), and the sequence was analyzed.

(12) Tissue Printing

Two sheets of filter paper were placed with the smooth surface facing upward, a leaf was placed thereon, and two sheets of filter paper were placed thereon so that the smooth surfaces faced the leaf. This assembly was struck with a hammer and the contents of the leaf were blotted onto the filter paper. After the filter paper was dried, the sheets were placed in a plastic container, 2□ TritonX-100 was added, and the container was shaken for 30 min at room temperature to remove chlorophyl and other pigments. Then a blocking treatment was performed by adding a PBST-skim milk solution (10 mM $NaPO_4$ (pH 7.2), 0.9% NaCl, 0.1% Tween-20, and 3% skim milk) and shaking the container for 30 min at room temperature.

Then an antibody treatment was performed by adding a 5,000-fold dilution of alkali phosphatase (AP)-labeled anti-CMV antibody in PBST-skim milk solution to the filter paper, and shaking for 1 hour at 37° C. Then the filter paper was washed by shaking for 5 min in PBST-skim milk solution. The washing procedure was repeated 3 times.

The filter paper was shaken for 5 min in AP buffer (0.1 M Tris-HCl (pH 9.5), 0.1 M NaCl, 5 mM $MgCl_2$) to remove the PBST-skim milk that had soaked into the filter paper, and then AP buffer was added and shaking was performed for 30 min to insure replacement with the buffer solution. Finally 10 mL of AP buffer containing 0.033% nitroblue tetrazolium (Wako Pure Chemical) and 0.0165% 5-bromo-4-chloro-3-indolyl phosphate (Wako Pure Chemical) was added, and the filter paper was shaken at room temperature to develop the color.

(13) Western Blotting

First leaves were pulverized together an amount of PBS (10 mM $NaPO_4$ (pH 7.2), 0.9% NaCl) equal to 5 times the weight of the leaves, and centrifuged at 12,000 rpm for 5 min. The supernatant was transferred to a separate tube, and an equivalent volume of the 2× sample buffer described below was added. After denaturing at 95° C. for 5 min, the sample was let stand at room temperature for 5 min, and then subjected to electrophoresis. Compact PAGE (Atto Corporation) was used for electrophoresis. The electrophoresis buffer was prepared by adding 90 mL of distilled water to 10 mL of the 10× running buffer described below.

Electrophoresis was carried out using a prepackaged 12.5% c-PAGEL™ electrophoresis gel (Atto Corporation), and after electrophoresis was completed, blotting was performed on a PVDF membrane (Millipore) using a Compact-BLOT (Atto Corporation). The PVDF membrane had been soaked several minutes in methanol beforehand, and then immersed in the blotting buffer described below. After blotting was completed, the membrane was placed in PBST-skim milk solution and shaken for 30 min, and then reacted with 1 μL of primary antibody diluted in 3 mL of PBST-skim milk solution for 1 hour in a Hybri-Bag™.

The membrane was washed three times in PBST-skim milk solution, and then reacted in a Hybri-Bag™ for 1 hour with 1 μl of AP-labeled anti-mouse antibody (Bio-Rad, Goat Anti- Mouse (H+L)-AP conjugate) diluted in 3 mL of PBST-skim milk solution. After washing the membrane in PBST-skim milk solution two times and in AP buffer two times, detection was performed using AP buffer containing 0.033% nitroblue tetrazolium and 0.0165% 5-bromo-4-chloro-3-indolyl phosphate. In addition, when HRP-labeled anti-mouse antibody (Amersham Biosciences; ECL Anti-mouse IgG, peroxidase-linked species-specific Whole antibody (from sheep)) or, HRP-labeled rabbit antibody (Sigma; anti-rabbit IgG (Whole molecule peroxidase conjugate)) was used as the secondary antibody, ECL-plus (GE Healthcare) was used.

For the primary antibody, an anti-His-Tag antibody (Novagen, His•Tag™ monoclonal antibody 0.2 mg/mL) was used to detect DxscFv and an anti-FLAG antibody (Sigma, ANTI-FLAG™ M2 monoclonal antibody) was used to detect DHFR. An anti-CMV-cp antibody (Japan Plant Protection Association) was used to detect the CMV.

2× sample buffer: 5 mL of 2-mercaptoethanol, 2 g of SDS, 5 g of sucrose, and 2 μg of bromophenol blue were added to 25 mL of 0.25 M Tris-HCl (pH 6.8), and the volume was raised to 50 mL with distilled water.

10× running buffer: Distilled water was added to 15.14 g of Tris, 72.067 g of glycine, and 5 g of SDS, and the volume was raised to 500 mL.

Blotting buffer: Distilled water was added to 0.604 g of Tris, 2.88 g of glycine, and 40 mL of methanol to raise the volume to 200 mL.

(14) Preparation of Virus not Expressing the CMV-Y 3a Protein

To prepare the vector lacking the 3a gene (3a-Stop), the CAA codon that encodes the amino acid glutamine at position 4 in the 3a protein of pCY3 was replaced with a TAA codon, which is a stop codon. FIG. 1 shows the insertion process. Using pCY3 as a template, PCR reactions were run with Y3-T7-5Bm and 3a-Stop-3 primers, and with 3a-Stop-5 and 3-3Hind primers.

After the amplification of both PCR products had been confirmed, a mixed solution containing 1 μL of each was used for the template, and PCR was performed again using Y3-T7-5Bm and Y3-3Hind primers, and the size of the PCR product was verified by electrophoresis. The product was treated with BamHI and HindIII, and the vector lacking the 3a gene was prepared by cloning at the BamHI and HindIII sites of pCY3.

(15) Insertion of DHFR Foreign Gene into CMV-Y RNA-2

The DHFR sequence was inserted between the StuI site and MluI region of a C2-H1 vector (Planta, Vol. 225, 277-286, 2007). FIG. 2 shows the process of inserting the foreign gene (DHFR) into the C2-H1 vector. With pEU-DHFR from the PROTEIOS™ Plasmid Set (Toyobo) as a template, PCR was performed using DHFR5 and DHFR-3Flg primers to obtain a DHFR gene having a FLAG tag and MluI site on the 3' end of DHFR. This was treated with MluI and cloned between the StuI site and MluI site of the C2-H1 vector.

(16) Insertion of DxscFv Foreign Gene into CMV-Y RNA-2

The DxscFv sequence was inserted between the StuI site and MluI region of a C2-H1 vector. FIG. 3 shows the process of inserting the foreign gene (DxscFv) into CMV-Y RNA2. PCR was conducted using pBE2113-DxscFv as a template to add an StuI site to the 5' end and an MluI site to the 3' end of the DxscFv ORF. Next, the DxscFv fragment was cloned to the StuI-MluI region of the C2-H1 vector to construct H1:DxscFv.

(17) Providing the 3a Protein Using the PVX-3a Vector and ClYVV-3a Vector

The 3a protein sequence from CMV-Y was inserted between the ClaI site and SalI region of a PVX vector (Plant J, Vol. 7, 1045-1053, 1995). PCR was carried out using pCY3 as a template with the Y3a-5Cl primer GCATCGATATGGCTTTCCAAGGTACCAG and the Y3a-3Xh primer CCGCTCGAGCTAAAGACCGTTAACCACCT to obtain a 3a gene fragment having ClaI and XhoI sites.

This was treated with ClaI and XhoI, and cloned to the ClaI and XhoI sites of the PVX vector. The resulting plasmids were treated with SpeI and linearized, transcribed in the same manner as the CMV clones, and used for inoculation. In addition, a 3a protein sequence from CMV-Y3a was inserted between the EcoRI site and SalI site region of a ClYVV vector (J Gen Plant Pathol, Vol. 69, 327-334, 2003).

PCR was conducted using pCY3 as a template with the Y3aLeco primer GGCTTTGAATTCATGGCTTTCCAAGGTACC and Y3aRsal primer CAGGTTGTCGACAAGACCGTTAACCACCTG to obtain a 3a gene fragment with EcoRI and SalI sites. This was cloned to the EcoRI and SalI sites of the ClYVV vector.

Because the ClYVV vector has a 35S promoter, inoculation was performed by directly rubbing the plasmid onto *Vicia faba* leaves with carborundum. Upper leaves wherein signs of the virus had been confirmed were used as an inoculum.

FIG. 4 shows the results of tissue printing using ClYVV-3a/Y1/Y2/3a-Stop and PVX-3a/Y1/Y2/3-a Stop. The former was inoculated into wild-type *N. bemthamiana* using leaves infected with ClYVV-3a, and about 3 weeks after inoculation, the plants were inoculated with the RNA transcript of Y1/Y2/3a-Stop, and 10 days later the CMV was detected by tissue printing.

In the latter a mixed inoculation of each RNA transcript was performed, and on day 5 post-inoculation (5 dpi) the CMV was detected by tissue printing. FIG. 5 shows the results of detecting DHFR and DxscFv by western blotting 6 to 12 days after mixed inoculation of wild-type *N. bemthamiana* using the PVX-3a/Y1/H1:DHFR (or H1:DxscFv)/3a-Stop RNA transcripts. Both results show that 3a was supplied in trans, and the foreign protein was expressed in the upper leaves of the plants inoculated with the virus vectors.

To verify that the CMV lacking the 3a gene did not reacquire 3a, RNA was extracted from the upper leaves, RT-PCR was conducted using Y3-T7-5Bm and Y3-3Hind primers, and the DNA fragment containing the 3a gene of the CMV was amplified. Direct sequencing of this fragment and the Y3-T7-5Bm primer were carried out to investigate the sequence at the site at which the mutation had been introduced, and it was confirmed that the stop codon had been retained.

(18) Preparation of 3a-Protein Transgenic *N. bemthamiana*

The sequence of the 3a protein from CMV-Y3a was inserted between the Xbal site and Sad site of pBE2113 (Plant Cell Physiology, Vol. 37, 49-59, 1996), which is a plant expression vector. FIG. 6 shows the process of inserting the cell movement protein (3a) into pBE2113.

PCR was conducted using pCY3 as a template, and the PCR amplification product (approximately 840 bp) was inserted into pGEM-TEasy (Promega). Next, the 3a fragment obtained by restriction enzyme treatments of the SpeI and SacI regions was inserted into the XbaI and Sad regions of pBE2113 to prepare the plant expression vector pBE2113-3a.

This was transduced into *Agrobacterium tumefaciens* LBA 4404 (Clontech) by a direct transduction method using freezing and thawing. Specifically *Agrobacterium tumefaciens* LBA 4404 was cultured in 50 mL of LB liquid medium (1% Bacto™ tryptone, 0.5% Bacto™ Yeast Extracts, 1% sodium chloride) in shaking culture at 28° C. until the $A_{600}$ absorption value reached approximately 1.0, and then cooled on ice. Centrifugal separation at 3,000 g and 4° C. was carried out to harvest the bacteria.

The bacterial cells were floated on 1 mL of an ice cold 20 mM calcium chloride solution, and 0.1 mL aliquots thereof were placed into Eppendorf tubes. Then 1 μg of recombinant plasmid pBE2113-3a was added, and the tubes were rapidly frozen in liquid nitrogen. Next, the resulting frozen cells were thawed at 37° C. and let stand for 5 min.

Next 1 mL of LB culture medium was added, and shaking culture was carried out at 28° C. for 2 to 4 hours. This was followed by centrifugal separation at approximately 10,000 g for 1 min, and the cells were harvested and floated on 0.1 mL of LB culture medium. The cells were then inoculated onto LB solid medium containing rifampicin (100 μg/mL), kanamycin (25 μg/mL) and streptomycin (300 μg/mL). The cells were cultured for 2 to 3 days at 28° C. to obtain transformant bacteria that had incorporated pBE2113-3a.

Shaking culture of the *Agrobacterium tumefaciens* LBA 4404 incorporating pBE2113-3a was carried out in LB liquid culture medium at 28° C., followed by centrifugal separation at 3,000 g and 4° C. The cells were harvested, floated on MS liquid culture medium [Physiol, Plant. 15:473 (1962)], and used in the plant transformation procedure. The transformation procedure was carried out by the leaf disk method using the recombinant *Agrobacterium* discussed above.

*Nicotiana benthamiana* leaves were sterilized for 15 min with 1% sodium hypochlorite solution, and washed 6 times with sterile distilled water. From the leaves 1 cm diameter circular leaf disks were cut out with a sterilized cork borer. The disks were immersed in the MS liquid culture medium suspension of *Agrobacterium tumefaciens* LBA 4404 carrying pBE2113-3a for 15 min.

After the disks were cultured at 28° C. for 3 days on MS solid medium [1 mg/L BAP (6-benzyl aminopurine) and 0.1 mg/L NAA (naphthalene acetic acid) with 3% sucrose, vitamin $B_5$, and 0.8% agar (pH 5.7)], they were washed with MS liquid culture medium containing antibiotics, 50 μg/mL kanamycin and 500 μg/mL carbenicillin (both Sigma). After the disks were washed, they were subcultured at two week intervals on the above antibiotic-containing MS solid medium (with 3% sucrose) at 25° C. (illumination for 16 hours, darkness for 8 hours). At weeks 4 to 8 of culturing calluses formed on the surfaces of the disks, and shoots were induced with additional subculturing.

The shoots were cut free from the roots, transplanted to the hormone-free MS solid culture medium [containing 3% sucrose, 50 μg/mL kanamycin, and 500 μg/mL carbenicillin (pH5.7)], and cultured. Plants that had rooted after 2 to 4 weeks were transplanted to potting soil in a closed-system, recombinant greenhouse, and raised to obtain next generation (T1) seeds.

(19) Raising of Transgenic Plants for Testing

The T1 seeds of the resulting 3a-transgenic plants were swelled in sterile water and subjected to a low-temperature treatment for 4 days at 4° C. After the surfaces of the seeds were sterilized for 5 min with a 1.5% sodium hypochlorite solution containing 0.02% TritonX-100, aseptic seeding was performed in ½ MS medium [with 1% sucrose, vitamin $B_5$, 1% agar (pH 5.7)] containing 125 mg/mL kanamycin. After incubation at 22° C. for 7 to 10 days, seedlings resistant to kanamycin were selected, transplanted to Jiffy-7 pellets, and grown in the closed-system, recombinant greenhouse.

(20) Expression of DxscFv by Supplying 3a Protein to 3a-Transgenic *N. benthamiana*

Figure 7:
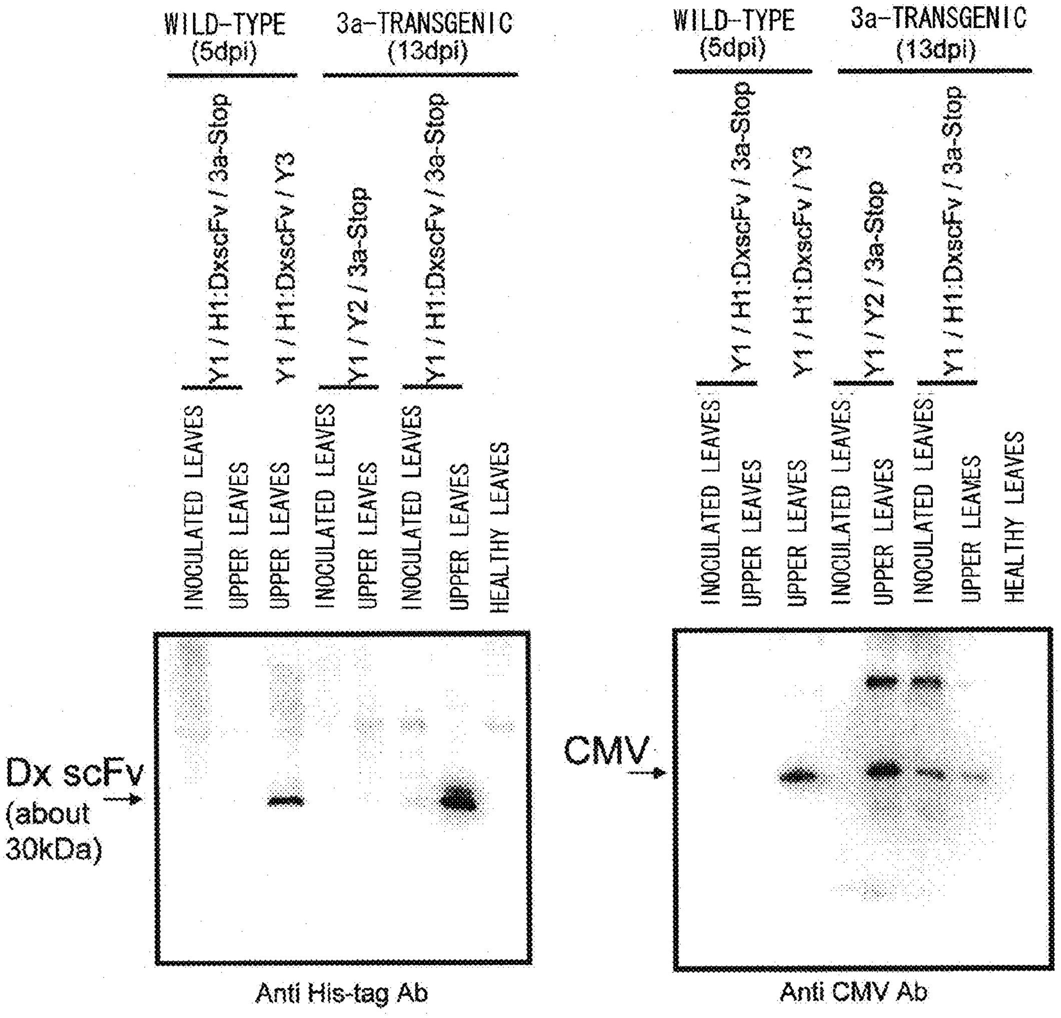
FIG. 7 shows the detection of DxscFv in wild type *Nicotiana benthamiana* and 3a-transgenic *Nicotiana benthamiana* after inoculation with Y1/H1:DxscFv/Y3 RNA. transcripts) or Y1/H1:DxscFv/3a-stop (RNA transcripts).

Wild-type and 3a-transgenic *N. benthamiana* plants were inoculated together with either the pCY1, pCY3, or 3a-Stop RNA transcripts that had been transcribed in vitro using the H1:DxscFv plasmid as a template. DxscFv expression was detected in infected leaves 5 days post-inoculation (dpi), and in both infected leaves and upper leaves 13 dpi using Western blotting. FIG. 7 shows the results of the detection of DxscFv in wild-type and in 3a-transgenic *N. benthamiana* after inoculation with Y1/H1: DxscFv/Y3 (RNA transcript) or Y1/H1: DxscFv/3a-stop (RNA transcript).

(21) Results

The expression of DxscFv was detected with western blotting in inoculated leaves on 5 dpi, and in both inoculated leaves and upper leaves on 13 dpi. Only slight expression was found in the inoculated leaves of 3a-transgentic plants inoculated with Y1/H1:DxscFv/3a-stop (RNA transcript), but extremely high amounts of DxscFv were detected in the upper leaves.

INDUSTRIAL APPLICABILITY

As disclosed above, the present invention relates to a non-diffusing plant virus vector. The present invention can provide a non-diffusing plant virus vector that enables avoidance of the risk of uncontrolled infection in host plants and unintended spread of a recombinant virus. In addition, because the virus vector can establish infection and proliferation only in recombinant plants transformed with a gene necessary for viral proliferation, the present invention can provide a novel recombinant plant system that can avoid the unintended spread of the virus. In addition, the present invention can provide a non-diffusing plant virus vector that cannot diffuse and spread on its own, but can establish systemic infection if the protein necessary for intercellular movement in the plant is supplied by separate means and functionality is imparted to the vector thereby. The present invention expands the scope of use of virus vectors because diffusion of the plant virus vector does not occur even if the same is used outdoors, etc. Proliferation of the virus vector and spread to other plants does not occur even when a recombinant plant is prepared using the plant virus vector. Therefore, the present invention is useful because it insures safety and makes the utilization of plant virus vectors more feasible.

The invention claimed is:

1. A non-diffusing plant virus vector being a cucumber mosaic virus (CMV) which:

lacks an RNA-3 gene encoding a 3a protein that is necessary for intercellular movement of the CMV genome in a plant via replacement of the CAA codon encoding the amino acid at the fourth position of the 3a protein with a stop codon, and thereby does not express the 3a protein; and contains a foreign gene inserted in RNA-2 of the CMV genome, which foreign gene is to be expressed in a plant;

the plant virus vector being capable of infecting and proliferating selectively and specifically in a transgenic plant which expresses the 3a protein.

2. A method for selective and specific expression of a foreign gene in a plant, which comprises combining providing a non-diffusing plant virus vector being a cucumber mosaic virus (CMV) vector which lacks the RNA-3 gene encoding a 3a protein that is necessary for intercellular movement of the CMV genome in a plant via replacement of the CAA codon encoding the amino acid at the fourth position of the 3a protein with a stop codon, and thereby does not express the 3a protein; and contains a foreign gene inserted in RNA-2 of the CMV genome;

providing a transgenic plant which expresses the 3a protein; and infecting the transgenic plant with the vector and proliferating the vector in the plant to thereby cause selective and specific expression of the foreign gene in the plant.

3. The method according to claim 2, wherein the transgenic plant which expresses the 3a protein is transformed with a recombinant vector containing the gene encoding the 3a protein.

4. The non-diffusing plant virus vector of claim 1, wherein the stop codon is TAA.

5. The method of claim 2, wherein the stop codon is TAA.

* * * * *

SEQUENCE LISTING

```
<160> NUMBER OF SEQ ID NOS: 22

<210> SEQ ID NO 1
<211> LENGTH: 28
<212> TYPE: DNA
<213> ORGANISM: Artificial Sequence
<220> FEATURE:
<223> OTHER INFORMATION: Primer based on Cucumber Mosaic Virus

<400> SEQUENCE: 1
```

-continued

```
gcatcgatat ggctttccaa ggtaccag                                       28


<210> SEQ ID NO 2
<211> LENGTH: 29
<212> TYPE: DNA
<213> ORGANISM: Artificial Sequence
<220> FEATURE:
<223> OTHER INFORMATION: Primer based on Cucumber Mosaic Virus

<400> SEQUENCE: 2

ccgctcgagc taaagaccgt taaccacct                                      29


<210> SEQ ID NO 3
<211> LENGTH: 30
<212> TYPE: DNA
<213> ORGANISM: Artificial Sequence
<220> FEATURE:
<223> OTHER INFORMATION: Primer based on Cucumber Mosaic Virus

<400> SEQUENCE: 3

ggctttgaat tcatggcttt ccaaggtacc                                     30


<210> SEQ ID NO 4
<211> LENGTH: 30
<212> TYPE: DNA
<213> ORGANISM: Artificial Sequence
<220> FEATURE:
<223> OTHER INFORMATION: Primer based on Cucumber Mosaic Virus

<400> SEQUENCE: 4

caggttgtcg acaagaccgt taaccacctg                                     30


<210> SEQ ID NO 5
<211> LENGTH: 45
<212> TYPE: DNA
<213> ORGANISM: Artificial Sequence
<220> FEATURE:
<223> OTHER INFORMATION: Primer based on Cucumber Mosaic Virus

<400> SEQUENCE: 5

cgggatccat taatacgact cactataggt aatctaacca cctgt                    45


<210> SEQ ID NO 6
<211> LENGTH: 20
<212> TYPE: DNA
<213> ORGANISM: Artificial Sequence
<220> FEATURE:
<223> OTHER INFORMATION: Primer based on Cucumber Mosaic Virus

<400> SEQUENCE: 6

ctggtacctt agaaagccat                                                20


<210> SEQ ID NO 7
<211> LENGTH: 20
<212> TYPE: DNA
<213> ORGANISM: Artificial Sequence
<220> FEATURE:
<223> OTHER INFORMATION: Primer based on Cucumber Mosaic Virus

<400> SEQUENCE: 7

atggctttct aaggtaccag                                                20


<210> SEQ ID NO 8
<211> LENGTH: 22
<212> TYPE: DNA
<213> ORGANISM: Artificial Sequence
```

<220> FEATURE:
<223> OTHER INFORMATION: Primer based on Cucumber Mosaic Virus

<400> SEQUENCE: 8
aacaagcttc ttatcatatt cc 22

<210> SEQ ID NO 9
<211> LENGTH: 19
<212> TYPE: DNA
<213> ORGANISM: Artificial Sequence
<220> FEATURE:
<223> OTHER INFORMATION: Primer based on Cucumber Mosaic Virus

<400> SEQUENCE: 9
atgatcagtc tgattgcgg 19

<210> SEQ ID NO 10
<211> LENGTH: 54
<212> TYPE: DNA
<213> ORGANISM: Artificial Sequence
<220> FEATURE:
<223> OTHER INFORMATION: Primer based on Cucumber Mosaic Virus

<400> SEQUENCE: 10
ggcacgcgtc acttgtcatc gtcgtccttg tagtcccgcc gctccagaat ctca 54

<210> SEQ ID NO 11
<211> LENGTH: 29
<212> TYPE: DNA
<213> ORGANISM: Artificial Sequence
<220> FEATURE:
<223> OTHER INFORMATION: Primer based on Cucumber Mosaic Virus

<400> SEQUENCE: 11
cgaggcctag aatgtacttg ggactgagc 29

<210> SEQ ID NO 12
<211> LENGTH: 30
<212> TYPE: DNA
<213> ORGANISM: Artificial Sequence
<220> FEATURE:
<223> OTHER INFORMATION: Primer based on Cucumber Mosaic Virus

<400> SEQUENCE: 12
gcgacgcgtt caaagttcat ccttatgatg 30

<210> SEQ ID NO 13
<211> LENGTH: 21
<212> TYPE: DNA
<213> ORGANISM: Artificial Sequence
<220> FEATURE:
<223> OTHER INFORMATION: Primer based on Cucumber Mosaic Virus

<400> SEQUENCE: 13
atggctttcc aaggtaccag t 21

<210> SEQ ID NO 14
<211> LENGTH: 45
<212> TYPE: DNA
<213> ORGANISM: Artificial Sequence
<220> FEATURE:
<223> OTHER INFORMATION: Primer based on Cucumber Mosaic Virus

<400> SEQUENCE: 14
cgggatccat taatacgact cactataggt aatctaacca cctgt 45

-continued

<210> SEQ ID NO 15
<211> LENGTH: 20
<212> TYPE: DNA
<213> ORGANISM: Artificial Sequence
<220> FEATURE:
<223> OTHER INFORMATION: Primer based on Cucumber Mosaic Virus

<400> SEQUENCE: 15
ctggtacctt agaaagccat 20

<210> SEQ ID NO 16
<211> LENGTH: 20
<212> TYPE: DNA
<213> ORGANISM: Artificial Sequence
<220> FEATURE:
<223> OTHER INFORMATION: Primer based on Cucumber Mosaic Virus

<400> SEQUENCE: 16
atggctttct aaggtaccag 20

<210> SEQ ID NO 17
<211> LENGTH: 22
<212> TYPE: DNA
<213> ORGANISM: Artificial Sequence
<220> FEATURE:
<223> OTHER INFORMATION: Primer based on Cucumber Mosaic Virus

<400> SEQUENCE: 17
aacaagcttc ttatcatatt cc 22

<210> SEQ ID NO 18
<211> LENGTH: 21
<212> TYPE: DNA
<213> ORGANISM: Artificial Sequence
<220> FEATURE:
<223> OTHER INFORMATION: Primer based on Cucumber Mosaic Virus

<400> SEQUENCE: 18
atggctttct aaggtaccag t 21

<210> SEQ ID NO 19
<211> LENGTH: 19
<212> TYPE: DNA
<213> ORGANISM: Artificial Sequence
<220> FEATURE:
<223> OTHER INFORMATION: Primer based on Cucumber Mosaic Virus

<400> SEQUENCE: 19
atgatcagtc tgattgcgg 19

<210> SEQ ID NO 20
<211> LENGTH: 54
<212> TYPE: DNA
<213> ORGANISM: Artificial Sequence
<220> FEATURE:
<223> OTHER INFORMATION: Primer based on Cucumber Mosaic Virus

<400> SEQUENCE: 20
ggcacgcgtc acttgtcatc gtcgtccttg tagtcccgcc gctccagaat ctca 54

<210> SEQ ID NO 21
<211> LENGTH: 29
<212> TYPE: DNA
<213> ORGANISM: Artificial Sequence
<220> FEATURE:
<223> OTHER INFORMATION: Primer based on Cucumber Mosaic Virus -continued

```
<400> SEQUENCE: 21

cgaggcctag aatgtacttg ggactgagc                                29


<210> SEQ ID NO 22
<211> LENGTH: 30
<212> TYPE: DNA
<213> ORGANISM: Artificial Sequence
<220> FEATURE:
<223> OTHER INFORMATION: Primer based on Cucumber Mosaic Virus

<400> SEQUENCE: 22

gcgacgcgtt caaagttcat ccttatgatg                               30
```